(12) United States Patent
Czyryca

(10) Patent No.: US 8,361,969 B2
(45) Date of Patent: Jan. 29, 2013

(54) DESIGNER CYCLIC PEPTIDES—HIV GP120 ANTAGONISTS AND THEIR APPLICATIONS

(76) Inventor: Przemyslaw Czyryca, Lehi, UT (US)

( * ) Notice: Subject to any disclaimer, the term of this patent is extended or adjusted under 35 U.S.C. 154(b) by 0 days.

(21) Appl. No.: 13/452,684

(22) Filed: Apr. 20, 2012

(65) Prior Publication Data

US 2012/0270806 A1    Oct. 25, 2012

Related U.S. Application Data

(60) Provisional application No. 61/478,152, filed on Apr. 22, 2011.

(51) Int. Cl.
| | |
|---|---|
| *A61K 38/00* | (2006.01) |
| *A61K 51/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |

(52) U.S. Cl. ........ 514/21.1; 514/1.1; 530/300; 530/333; 424/1.69

(58) Field of Classification Search ........................ None
See application file for complete search history.

(56) References Cited

FOREIGN PATENT DOCUMENTS

WO    WO2008143679 A1 *  11/2008

\* cited by examiner

*Primary Examiner* — Maury Audet

(57) ABSTRACT

The present invention is concerned with a novel composition of matter—a cyclic peptide derived from computer modeling studies that modulates the structure and function of the HIV main envelope protein gp120. The compound is capable of binding to the CD4-binding region of gp120 (this defines it as a CD4 mimic), and can be used for the purposes of: (1) controlling and preventing HIV infections, (2) detecting, isolating and purifying gp120. Contrary to examples of prior art that involved CD4 mimics being either small molecules or macromolecules, the present invention is concerned with the class of "large small molecules" that may offer a satisfactory balance between the activity and drug-like properties. Modified variants of the prototype compound that can be reasonably considered its derivatives are also claimed.

1 Claim, 2 Drawing Sheets

INHIBITION OF X4-TROPIC HIV-1 ATTACHMENT BY ASTX-60-1-d1

| RLU (Relative Light Units) | | | | | | | |
|---|---|---|---|---|---|---|---|
| CONC (µM) | 0.00 | 0.032 | 0.16 | 0.8 | 4.0 | 20.0 | 100.0 |
| SAMPLE 1 | 59233.4 | 60719.7 | 56853.5 | 58939.4 | 57794.1 | 43846.9 | 20740.7 |
| SAMPLE 2 | 60110.3 | 58177.6 | 50709.5 | 56438.1 | 49465.8 | 39375.0 | 17908.2 |
| SAMPLE 3 | 60896.9 | 53692.9 | 56382.4 | 56318.7 | 55518.1 | 44041.6 | 21493.9 |
| MEAN | 60080.2 | 57530.1 | 54648.5 | 57232.1 | 54259.4 | 42421.2 | 20047.6 |
| % VC | 100.0 | 95.8 | 91.0 | 95.3 | 90.3 | 70.6 | 33.4 |
| STD DEV | 1.4 | 5.9 | 5.7 | 2.5 | 7.2 | 4.4 | 3.1 |

| TOXICITY VALUES (CellTiter96 - O. D. @ 490/650 nm) | | | | | | | |
|---|---|---|---|---|---|---|---|
| CONC (µM) | 0.00 | 0.032 | 0.16 | 0.8 | 4.0 | 20.0 | 100.0 |
| SAMPLE 1 | 1.205 | 1.216 | 1.219 | 1.202 | 1.254 | 1.255 | 1.236 |
| SAMPLE 2 | 1.207 | 1.180 | 1.198 | 1.231 | 1.231 | 1.258 | 1.232 |
| SAMPLE 3 | 1.195 | 1.202 | 1.217 | 1.239 | 1.236 | 1.254 | 1.222 |
| MEAN | 1.202 | 1.199 | 1.211 | 1.224 | 1.240 | 1.255 | 1.230 |
| % CC | 100.0 | 99.7 | 100.7 | 101.8 | 103.2 | 104.4 | 102.3 |
| STD DEV | 0.5 | 1.5 | 1.0 | 1.6 | 1.0 | 0.2 | 0.6 |

IC50 (µM) = 48.7   TC50 (µM) = >100.0   TI = >2.05
IC90 (µM) = >100.0

X4-Tropic Attachment Inhibition Assay
January 4, 2012    Cells: Magi R5    Southern Research Institute
Tech: Snyder    Virus: IIIB    Project: 13210.03

INHIBITION OF X4-TROPIC HIV-1 ATTACHMENT BY 2-s4-98rp-39m-60-1m1_MC

| RLU (Relative Light Units) | | | | | | | |
|---|---|---|---|---|---|---|---|
| CONC (µM) | 0.00 | 0.316 | 1.0 | 3.16 | 10.0 | 31.6 | 100.0 |
| SAMPLE 1 | 41508.6 | 44225.5 | 60669.9 | 43291.2 | 22817.6 | 16165.2 | 3302.8 |
| SAMPLE 2 | 40957.0 | 35305.8 | 40657.9 | 29837.5 | 28521.0 | 13170.0 | 3066.6 |
| SAMPLE 3 | 41309.6 | 38738.1 | 41844.8 | 77863.4 | 25890.1 | 18710.3 | 3567.9 |
| MEAN | 41258.4 | 39423.1 | 47724.2 | 50330.7 | 25742.9 | 16015.2 | 3312.4 |
| % VC | 100.0 | 95.6 | 115.7 | 122.0 | 62.4 | 38.8 | 8.0 |
| STD DEV | 0.7 | 10.9 | 27.2 | 60.0 | 6.9 | 6.7 | 0.6 |

| TOXICITY VALUES (CellTiter96 - O. D. @ 490/650 nm) | | | | | | | |
|---|---|---|---|---|---|---|---|
| CONC (µM) | 0.00 | 0.316 | 1.0 | 3.16 | 10.0 | 31.6 | 100.0 |
| SAMPLE 1 | 1.441 | 1.221 | 1.390 | 1.346 | 1.464 | 1.375 | 1.480 |
| SAMPLE 2 | 1.305 | 1.179 | 1.204 | 1.244 | 1.205 | 1.041 | 1.050 |
| SAMPLE 3 | 1.181 | 1.308 | 1.301 | 1.205 | 1.194 | 1.611 | 1.066 |
| MEAN | 1.309 | 1.236 | 1.298 | 1.265 | 1.288 | 1.342 | 1.199 |
| % CC | 100.0 | 94.5 | 99.2 | 96.7 | 98.4 | 102.6 | 91.6 |
| STD DEV | 9.9 | 5.0 | 7.1 | 5.6 | 11.7 | 21.9 | 18.6 |

IC50 (µM) = 18.3  TC50 (µM) = >100.0  TI = >5.46

IC90 (µM) = 92.9

X4-Tropic Attachment Inhibition Assay
October 5, 2010    Cells: Magi R5    Southern Research Institute
Tech: Snyder    Virus: IIIB    Project: 13210.01

SEQUENCE LISTING

```
<160> NUMBER OF SEQ ID NOS: 3

<210> SEQ ID NO 1
<211> LENGTH: 14
<212> TYPE: PRT
<213> ORGANISM: artificial sequence
<220> FEATURE:
<223> OTHER INFORMATION: designer CD4 mimic, HIV gp120 antagonist
<220> FEATURE:
<221> NAME/KEY: MOD_RES
<222> LOCATION: (3)..(3)
<223> OTHER INFORMATION: D-Asp
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (6)..(6)
<223> OTHER INFORMATION: D-Tyr
<220> FEATURE:
<221> NAME/KEY: MOD_RES
<222> LOCATION: (7)..(7)
<223> OTHER INFORMATION: D-Glu
<220> FEATURE:
<221> NAME/KEY: MOD_RES
<222> LOCATION: (9)..(9)
<223> OTHER INFORMATION: D-Pro
<220> FEATURE:
<221> NAME/KEY: MOD_RES
<222> LOCATION: (10)..(10)
<223> OTHER INFORMATION: D-biphenylalanine
<220> FEATURE:
<221> NAME/KEY: MOD_RES
<222> LOCATION: (11)..(11)
<223> OTHER INFORMATION: D-Asp
<220> FEATURE:
<221> NAME/KEY: site
<222> LOCATION: (1)..(14)
<223> OTHER INFORMATION: Head-to-tail cyclization

<400> SEQUENCE: 1

Ile Ile Xaa Xaa Lys Xaa Xaa Gly Xaa Xaa Xaa Asp Phe Asp
1               5                   10

<210> SEQ ID NO 2
<211> LENGTH: 14
<212> TYPE: PRT
<213> ORGANISM: artificial sequence
<220> FEATURE:
<223> OTHER INFORMATION: designer CD4 mimic, HIV gp120 antagonist
<220> FEATURE:
<221> NAME/KEY: MOD_RES
```

```
<222> LOCATION: (3)..(3)
<223> OTHER INFORMATION: D-Asp
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (6)..(6)
<223> OTHER INFORMATION: D-Tyr
<220> FEATURE:
<221> NAME/KEY: MOD_RES
<222> LOCATION: (7)..(7)
<223> OTHER INFORMATION: D-Glu
<220> FEATURE:
<221> NAME/KEY: MOD_RES
<222> LOCATION: (9)..(9)
<223> OTHER INFORMATION: D-Pro
<220> FEATURE:
<221> NAME/KEY: MOD_RES
<222> LOCATION: (10)..(10)
<223> OTHER INFORMATION: D-phenylalanine
<220> FEATURE:
<221> NAME/KEY: MOD_RES
<222> LOCATION: (11)..(11)
<223> OTHER INFORMATION: D-Asp
<220> FEATURE:
<221> NAME/KEY: site
<222> LOCATION: (1)..(14)
<223> OTHER INFORMATION: Head-to-tail cyclization

<400> SEQUENCE: 2

Ile Ile Xaa Xaa Lys Xaa Xaa Gly Xaa Xaa Xaa Asp Phe Asp
1               5                   10

<210> SEQ ID NO 3
<211> LENGTH: 14
<212> TYPE: PRT
<213> ORGANISM: artificial sequence
<220> FEATURE:
<223> OTHER INFORMATION: designer CD4 mimic, HIV gp120 antagonist
<220> FEATURE:
<221> NAME/KEY: MOD_RES
<222> LOCATION: (3)..(3)
<223> OTHER INFORMATION: D-Ser
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (6)..(6)
<223> OTHER INFORMATION: D-Tyr
<220> FEATURE:
<221> NAME/KEY: MOD_RES
<222> LOCATION: (7)..(7)
<223> OTHER INFORMATION: D-Glu
<220> FEATURE:
<221> NAME/KEY: MOD_RES
<222> LOCATION: (9)..(9)
<223> OTHER INFORMATION: D-Pro
<220> FEATURE:
<221> NAME/KEY: MOD_RES
<222> LOCATION: (10)..(10)
<223> OTHER INFORMATION: D-biphenylalanine
<220> FEATURE:
<221> NAME/KEY: MOD_RES
<222> LOCATION: (11)..(11)
<223> OTHER INFORMATION: D-Asp
<220> FEATURE:
<221> NAME/KEY: site
<222> LOCATION: (1)..(14)
<223> OTHER INFORMATION: Head-to-tail cyclization
```

```
<400> SEQUENCE: 3

Pro Ile Xaa Xaa Lys Xaa Xaa Gly Xaa Xaa Xaa Asp Phe Asp
1               5                   10
```

DESIGNER CYCLIC PEPTIDES—HIV GP120 ANTAGONISTS AND THEIR APPLICATIONS

CROSS-REFERENCES TO RELATED APPLICATIONS

This application claims the benefits of an earlier provisional application No. 61/478,152, filed on Apr. 22, 2001.

STATEMENT REGARDING FEDERALLY SPONSORED RESEARCH OR DEVELOPMENT

The present invention was made with government support under grant #1013428 awarded by the National Science Foundation. The government has certain rights in the invention.

THE NAMES OF THE PARTIES TO A JOINT RESEARCH AGREEMENT.

Not Applicable

INCORPORATION-BY-REFERENCE OF MATERIAL SUBMITTED ON A COMPACT DISC.

Machine-readable peptide sequence listing has been uploaded through EFS-Web

BACKGROUND OF THE INVENTION

1. Field of the Invention

The present invention is concerned with a novel composition of matter—a designer, cyclic peptide that modulates the structure and function of the HIV main envelope protein gp120. The invention is related to the fields of medicinal chemistry, biochemistry and virology.

2. Description of Related Art

HIV-1—the virus responsible for the AIDS pandemic, infects the host's cells by means of receptor-assisted endocytosis. The viral glycoprotein gp120 and the cell's CD4 protein are implicated in the initial stage of attachment of the virus to the cell (Kwong et al. 1998). Following this initial attachment, gp120 undergoes a major conformational rearrangement (Myszka et al. 2000), exposing the chemokine co-receptor binding site and triggering subsequent stages of the fusion process, (Wyatt and Sodroski, 1998).

Haim et al., 2009, have shown that the inhibition of HIV-1 virus by the soluble form of CD4 (sCD4) and its certain less active, small molecule mimics, occurs due to premature triggering of the conformational change in gp120. The activated state of gp120, primed for binding to the co-receptor, is transient and its life span is measured in minutes. Afterward, it undergoes a further, irreversible conformational change, leading to a loss of binding competency. The induction of the activated conformation of gp120 by soluble CD4 mimics (SCMs) causes a moderate increase of the CD4-independent HIV infectivity at certain SCM concentrations range. At higher concentrations, the inhibitory effect is predominant. The possibility to trigger premature, spontaneous and irreversible deactivation of the viral protein responsible for the infectivity, by targeting the highly conserved region of this protein, is an elegant and attractive paradigm for the development of anti-HIV therapeutics, especially considering the independence of such drugs on the co-receptor tropism of particular HIV strains.

In addition to their role as antiviral drugs, SCMs have the potential to be used as immunostimulants, either amplifying the natural immune response, or the response induced by anti-HIV vaccines. This potential results from the observations that CD4-independent strains of HIV have an increased susceptibility to neutralizing antibodies (Kolchinsky et al. 1999, Kolchinsky et al. 2001, Thomas et al. 2003). This independency is caused by the exposure of the normally hidden epitopes that are responsible for co-receptor binding. Both sCD4 and SCMs cause precisely this effect: they trigger the conformational change of gp120 and expose the CD4-induced epitopes. Thus, in addition to being classical entry inhibitors, SCMs are expected to increase the susceptibility of the virus to the immune response of the infected organism.

Before the above-described mechanism of gp120 inhibition by sCD4 and SCMs has been recognized, it was speculated that the inhibition may occur due to competitive binding or via triggering the shedding of gp120, but regardless of the mechanism, efforts were undertaken to develop gp120-modulating molecules. While no SCMs currently are on the market, several compounds are at different stages of development. Relevant references include: include: Zhao et al. 2005, Stricher et al. 2008, Lin et al. 2003.

While the general purpose to controlling HIV infections, and the chemical nature of the compounds disclosed in the present invention makes them related to retrocyclins (Cole et al. 2002), it should be noted that retrocyclins are CD4 antagonists, whereas the compounds that the present patent application is concerned with, are, by their design, gp120 antagonists.

REFERENCES

Cole A M, Hong T, Boo L M, Nguyen T, Zhao C, Bristol G, Zack J A, Waring A J, Yang O O, Lehrer R I. "Retrocyclin: a primate peptide that protects cells from infection by T- and M-tropic strains of HIV-1" *Proc. Natl. Acad. Sci. USA*. (2002) Feb 19;99(4):1813-8.

Haim H, Si Z, Madani N, Wang L, Courter J R, Princiotto A, Kassa A, DeGrace M, McGee-Estrada K, Mefford M, Gabuzda D, Smith A B 3rd, Sodroski J. "Soluble CD4 and CD4-Mimetic Compounds Inhibit HIV-1 Infection by Induction of a Short-Lived Activated State." *PLoS Pathog*. (2009) 5(4): e1000360

Kolchinsky P, Mirzabekov T, Farzan M, Kiprilov E, Cayabyab M, Mooney L J, et al. "Adaptation of a CCR5-using, primary human immunodeficiency virus type 1 isolate for CD4-independent replication." *J. Virol*. (1999), 73:8120 8126.

Kolchinsky P, Kiprilov E, Sodroski J. "Increased neutralization sensitivity of CD4-independent human immunodeciency virus variants." *J. Virol*. (2001), 75:2041 2050.

Kwong P D, Wyatt R, Robinson J, Sweet R, Sodroski J and Hendrickson W. "Structure of an HIV-1 gp120 envelope glycoprotein in complex with the CD4 receptor and a neutralizing human antibody." Nature, (1998) 393:649-59.

Lackman-Smith, C. Osterling, C. Luckenbaugh, K., Mankowski, M. Snyder, B., Lewis, G., Paull, J. Profy, A., Ptak, R. G. Buckheit, Jr., W. W., Watson, K., M, Cummins, Jr., J. E., and Sanders-Beer, B. E., "Development of a Comprehensive Human Immunodeficiency Virus Type 1 Screening Algorithm for Discovery and Preclinical Testing of Topical Microbicides"*Antimicrob. Agents Chemother*. (2008) 52,1768-1781

Lin P F, Blair W, Wang T, Spicer T, Guo Q, Zhou N, Gong Y F, Wang H G, Rose R, Yamanaka G, Robinson B, Li C B, Fridell R, Deminie C, Demers G, Yang Z, Zadjura L, Meanwell N, Colonno R. "A small molecule HIV-1 inhibitor that targets the HIV-1 envelope and inhibits CD4 receptor binding." *Proc. Natl. Acad. Sci. USA*. (2003) Sep. 16;100(19): 11013-8

Merrifield R B "Solid Phase Peptide Synthesis. I. The Synthesis of a Tetrapeptide". *J. Am. Chem. Soc.* (1963) 85 (14): 2149-2154.

Metropolis, N. and Ulam, S. "The Monte Carlo Method." *J. Amer. Stat. Assoc.* (1949) 44, 335-341

Myszka D G, Sweet RW, Hensley P, Brigham-Burke M, Kwong P D, Hendrickson W A, Wyatt R, Sodroski J, Doyle M L "Energetics of the HIV gp120-CD4 binding reaction." *Proc. Natl. Acad. Sci. USA* (2000) 97: 9026-9031.

Schneider, G., Fechner, U. "Computer-based de novo design of drug-like molecules", *Nature Reviews Drug Discovery* (2005) 4, 649-663.

Stricher F, Huang C C, Descours A, Duquesnoy S, Combes O, Decker J M, Kwon Y D, Lusso P, Shaw G M, Vita C, Kwong P D, Martin L. "Combinatorial optimization of a CD4-mimetic miniprotein and cocrystal structures with HIV-1 gp120 envelope glycoprotein." *J. Mol. Biol.* (2008) Oct 3;382(2):510-24

Thomas E R, Shotton C, Weiss R A, Clapham P R, McKnight A. "CD4-dependent and CD4-independent HIV-2: consequences for neutralization." *AIDS* (2003), 17:291 300.

Wyatt R, Sodroski J "The HIV-1 envelope glycoproteins: fusogens, antigens, and immunogens." *Science* (1998) 280: 1884-1888.

Zhao Q, Ma L, Jiang S, Lu H, Liu S, He Y, Strick N, Neamati N, Debnath A K. "Identification of N-phenyl-N'-(2,2,6,6-tetramethyl-piperidin-4-yl)-oxalamides as a new class of HIV-1 entry inhibitors that prevent gp120 binding to CD4" *Virology* (2005) Sep. 1;339(2):213-25.

BRIEF SUMMARY OF THE INVENTION

The present invention is concerned with a designer cyclic peptide, assigned the symbol 2-s4-98rp-39m-60-1_MC, and with similar compounds that can reasonably be considered its derivatives. This peptide is a soluble CD4 mimic (SCM), and it inhibits the HIV-1 entry by ligating the CD4-binding region of gp120, with the IC50=<1.64 µM. No cytotoxicity has been observed up to the highest tested concentration of 100 µM.

The invention encompasses the novel composition of matter and the methods of applying thereof to controlling or preventing the infection with the HIV virus, to the development and application of vaccines against HIV, to the detection of the HIV virus, and to the purification of gp120-related biological material.

The present invention has been made through computer modeling (de novo design). There is no relation of the present invention to either prior art or to natural compounds. The origins of the invention define what compounds can reasonably be considered derivatives of 2-s4-98rp-39m-60-1_MC, and how broad the claims can be. Due to the completely artificial origins of the compound, and because 2-s4-98rp-39m-60-1_MC comprises D-amino acids, an independent discovery of similar compounds is highly unlikely, and such similar compounds should be considered derivative works.

DETAILED DESCRIPTION OF THE INVENTION

Compound 2-s4-98rp-39m-60-1_MC—a Novel Composition of Matter

Figure 1:
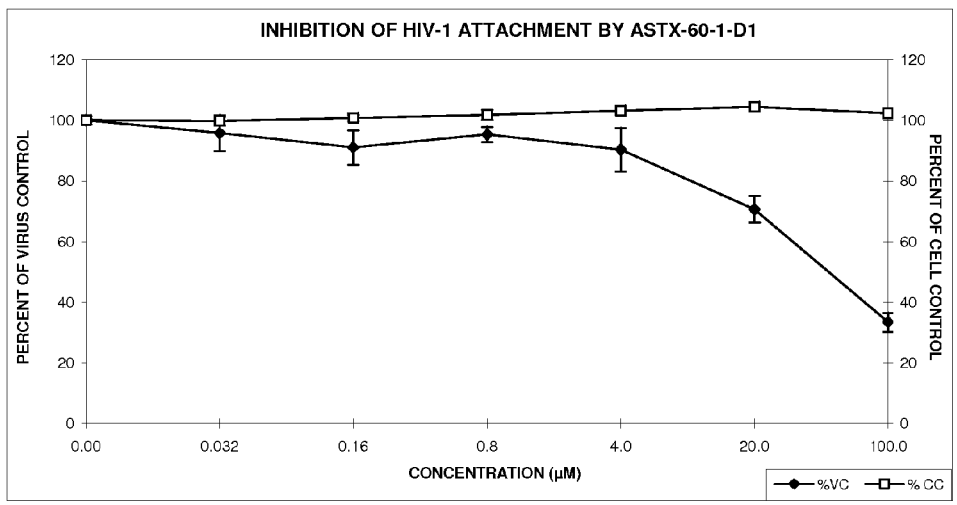
FIG. 1. Chemical structure of compound 2-s4-98rp-39m-60-1_MC
Figure 2:
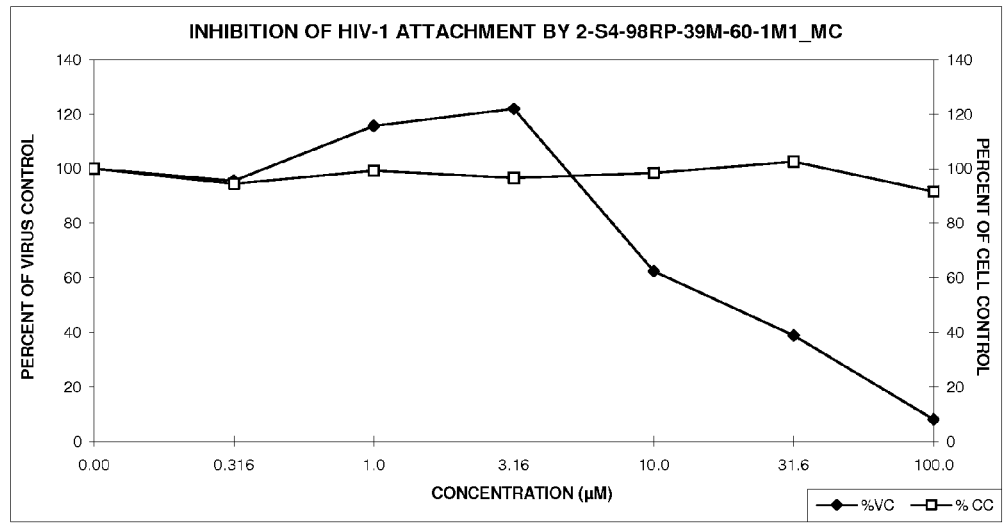
FIG. 2. Results of the testing of compound 2-s4-98rp-39m-60-1_MC in an attachment assay.
Figure 1:
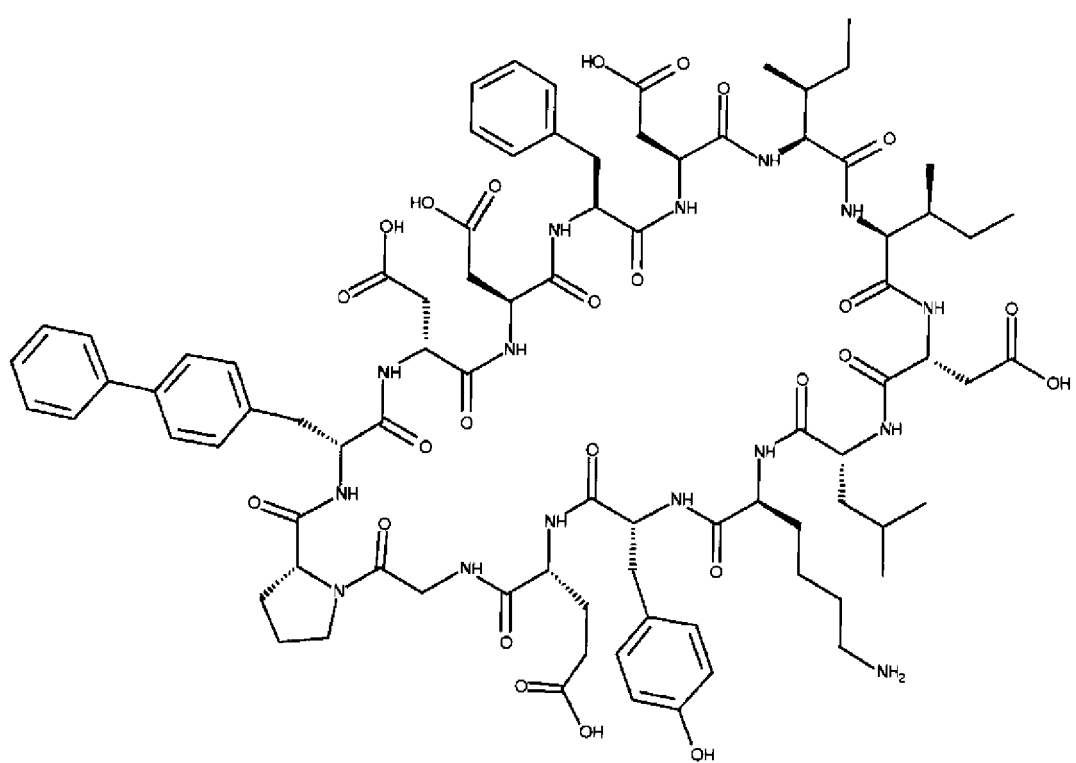
Figure 2:
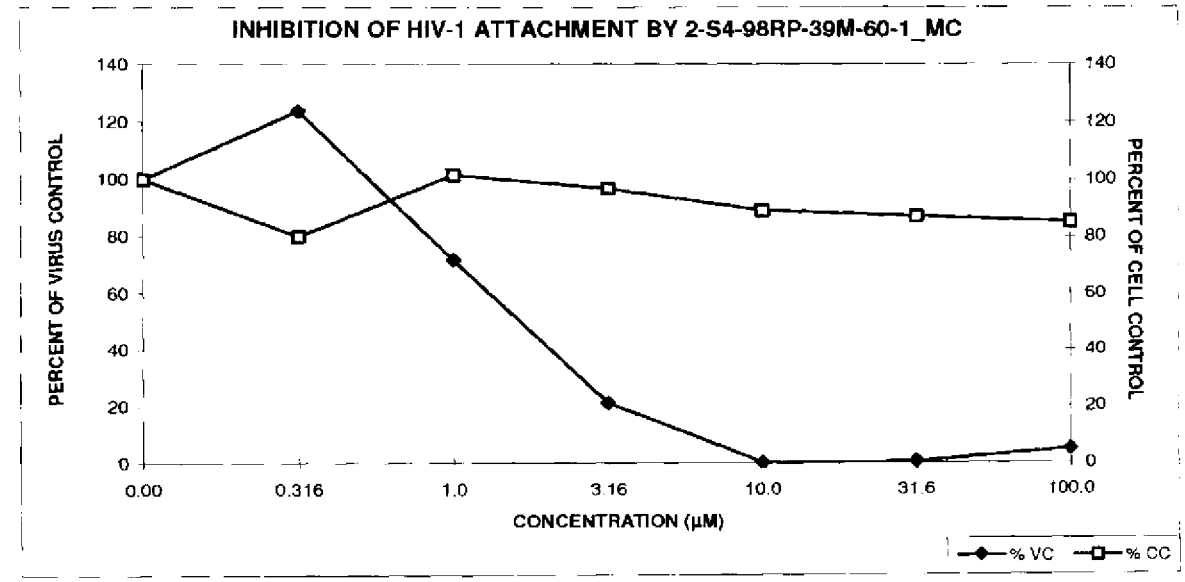

The present invention relates to peptide 2-s4-98rp-39m-60-1_MC, comprising the following sequence of 14 amino acids, and cyclized head-to-tail:
where:
$Xaa^a$=D-Asp
$Xaa^b$=D-Leu
$Xaa^c$=D-Tyr
$Xaa^d$=D-Glu
$Xaa^e$=D-Pro
$Xaa^f$=D-Biphenylalanine
$Xaa^g$=D-Asp Compound 2-s4-98rp-39m-60-1_MC was designed via a de novo computational process (Metropolis and Ulam, 1949; see also a review by Schneider and Fechner, 2005) to interact with the CD4-binding region of gp120. The specific features of the design algorithm are not claimed, and they are protected as a trade secret. The structure of peptide 2-s4-98rp-39m-60-1_MC is shown in FIG. 1, and its sequence provided as sequence No. 1 in the machine-readable sequence listing. Additionally, compounds obtained through modifications of the above sequence can rationally be considered derivatives of the above sequence, and are also related to the present invention. Such modifications can involve: (i) deletion or substitution of a small number of amino acids within the sequence, or (ii) incorporation of the complete or truncated sequence of 2-s4-98rp-39m-60-1_MC into a larger molecule, or (iii) derivatization of the side chains of the amino acids comprising the sequence of 2-s4-98rp-39m-60-1_MC.

Specifically, two such derivatives have been designed, synthesized and tested. They exhibit a moderate activity as attachment inhibitors, in the double-digit micromolar range. Their sequences are provided in the accompanying machine-readable sequence listings as No. 2 and No. 3.

Synthesis of 2-s4-98rp-39m-60-1_MC

Compound 2-s4-98rp-39m-60-1_MC has been synthesized using the routine solid phase methodology for peptide synthesis, involving the immobilization of the first amino acid on a polymeric carrier, followed by iterative de-blocking and coupling with subsequent amino acids. The final cyclization was carried out while the linear peptide was still attached to the polymeric carrier. GC-MS was used to confirm the compound's molecular mass. The compounds was purified using HPLC to 95% purity. The methods for solid phase peptide synthesis have been widely known and routinely applied since the 1960s (Merrifield, 1963). They arguably do not need to be presented in more detail to enable any person of ordinary skill in the pertinent art to make and use the invention.

Testing of Compound 2-s4-98rp-39m-60-1_MC

Compound 2-s4-98rp-39m-60-1_MC has been tested at the Southern Research institute, in a commercial screening program. An attachment assay, described by Lackman-Smith et al., 2008, was used. The test results are presented in FIG. 2. The observed IC50 of 1.64 μM represents the lower boundary of the actual activity, due to the fact that the assay has been optimized for screening co-receptor antagonists—the tested compounds are pre-equilibrated with the cells, rather than with the virus. CD4 mimics—gp120 antagonists are unable to equilibrate with their molecular target within such protocol.

Uses of Compound 2-s4-98rp-39m-60-1_MC or its Derivatives

Compound 2-s4-98rp-39m-60-1_MC or its derivatives can be used alone or in combination with other antiviral drugs for the purpose of controlling infections caused by the HIV virus, or for preventing such infections. The route of administration may involve injection, transdermal or oral delivery of the compound or its mixture with other ingredients, either in the solid phase, or in a solution. In the preventive role, 2-s4-98rp-39m-60-1_MC or its derivatives can also be the active ingredients (or one of several active ingredients) of topical formulations.

The mechanism of action of compound 2-s4-98rp-39m-60-1_MC, that involves causing a conformational rearrangement of gp120 and exposure of CD4-induced epitopes, responsible for co-receptor binding, offers the possibility of employing compound 2-s4-98rp-39m-60-1_MC or its derivatives as specific immunostimulants. In this role, compound 2-s4-98rp-39m-60-1_MC or its derivatives should be administered in a manner already described in the context of their use as antiviral drugs, to either promote the natural response of the immune system to the presence of the virus, or to augment the response to the epitopes involved in co-receptor binding induced by a vaccine.

In addition to the therapeutic role, compound 2-s4-98rp-39m-60-1_MC or its derivatives can be used for the purpose of detecting the presence of the HIV virus. The ability of the compound to bind to the viral protein gp120 can be utilized by tethering the compounds to appropriate polymeric matrices and thus creating materials with their physicochemical properties dependent upon the formation of the complex between 2-s4-98rp-39m-60-1_MC and the viral gp120. Such materials can be then used as specific molecular recognition elements in biosensors. A related application of materials based on 2-s4-98rp-39m-60-1_MC involves using these materials for the purpose of affinity chromatography, allowing for isolation and purification of gp120, or gp120-containing assemblies from biological materials.

The invention claimed is:

1. A cyclic peptide, comprising the following sequence: cyclo(Ile-Ile-Xaa$^a$-Xaa$^b$-Lys-Xaa$^c$-Xaa$^d$-Gly-Xaa$^e$-Xaa$^f$-Xaa$^g$-Asp-Phe-Asp)(SEQ ID NO:1)

where:
Xaa$^a$=D-Asp
Xaa$^b$=D-Leu
Xaa$^c$=D-Tyr
Xaa$^d$=D-Glu
Xaa$^e$=D-Pro
Xaa$^f$=D-Biphenylalanine
Xaa$^g$=D-Asp;

or a cyclic derivative (at least 93% sequence identity), in which any single amino acid is replaced by a chemical building block; wherein the peptide or derivative inhibits HIV-1 attachment to CD4-expressing cells.

* * * * *

UNITED STATES PATENT AND TRADEMARK OFFICE
CERTIFICATE OF CORRECTION

| | |
|---|---|
| PATENT NO. | : 8,361,969 B2 |
| APPLICATION NO. | : 13/452684 |
| DATED | : January 29, 2013 |
| INVENTOR(S) | : Przemyslaw Czyryca |

It is certified that error appears in the above-identified patent and that said Letters Patent is hereby corrected as shown below:

Delete Drawings Sheets 1 and 2 and substitute therefore the attached Drawing Sheets 1 and 2.

Signed and Sealed this
Nineteenth Day of March, 2013

Teresa Stanek Rea
*Acting Director of the United States Patent and Trademark Office*

INHIBITION OF X4-TROPIC HIV-1 ATTACHMENT BY 2-s4-98rp-39m-60-1_MC

| RLU (Relative Light Units) | | | | | | | |
|---|---|---|---|---|---|---|---|
| CONC (µM) | 0.00 | 0.316 | 1.0 | 3.16 | 10.0 | 31.6 | 100.0 |
| SAMPLE 1 | 41508.6 | 27193.9 | 45993.1 | 12956.2 | 0.0 | 603.2 | 5883.0 |
| SAMPLE 2 | 40957.0 | 50240.4 | 19673.0 | 3399.7 | 0.0 | 0.0 | 179.3 |
| SAMPLE 3 | 41309.6 | 75666.6 | 23243.7 | 9782.1 | 194.6 | 0.0 | 0.0 |
| MEAN | 41258.4 | 51033.6 | 29636.6 | 8712.7 | 64.9 | 201.1 | 2020.8 |
| % VC | 100.0 | 123.7 | 71.8 | 21.1 | 0.2 | 0.5 | 4.9 |
| STD DEV | 0.7 | 58.8 | 34.6 | 11.8 | 0.3 | 0.8 | 8.1 |

| TOXICITY VALUES (CellTiter96 - O. D. @ 490/650 nm) | | | | | | | |
|---|---|---|---|---|---|---|---|
| CONC (µM) | 0.00 | 0.316 | 1.0 | 3.16 | 10.0 | 31.6 | 100.0 |
| SAMPLE 1 | 1.441 | 0.933 | 1.304 | 1.162 | 0.986 | 1.114 | 1.204 |
| SAMPLE 2 | 1.305 | 1.228 | 1.360 | 1.234 | 1.319 | 1.156 | 0.985 |
| SAMPLE 3 | 1.181 | 0.979 | 1.323 | 1.404 | 1.198 | 1.151 | 1.153 |
| MEAN | 1.309 | 1.047 | 1.329 | 1.267 | 1.167 | 1.140 | 1.114 |
| % CC | 100.0 | 80.0 | 101.5 | 96.8 | 89.2 | 87.1 | 85.1 |
| STD DEV | 9.9 | 12.1 | 2.2 | 9.5 | 12.9 | 1.8 | 8.7 |

IC50 (µM) = 1.64    TC50 (µM) = >100.0    TI = >60.98

IC90 (µM) = 5.82

X4-Tropic Attachment Inhibition Assay
Cells: Magi R5
Virus: IIIB

October 5, 2010
Tech: Snyder

Southern Research Institute
Project: 13210.01